(12) United States Patent
Mahanpour et al.

(10) Patent No.: US 6,866,416 B1
(45) Date of Patent: Mar. 15, 2005

(54) DETECTING HEAT GENERATING FAILURES IN UNPASSIVATED SEMICONDUCTOR DEVICES

(75) Inventors: Mehrdad Mahanpour, Union City, CA (US); Alice H. Choi, Mountain View, CA (US); Mohammad Massoodi, Los Altos, CA (US); Boon-Yong Ang, Cupertino, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 10/635,996

(22) Filed: Aug. 7, 2003

(51) Int. Cl.[7] .............................................. G01N 25/00
(52) U.S. Cl. ............................................. 374/57; 374/7
(58) Field of Search ............................. 374/4, 5, 7, 29, 374/30, 43, 44, 45, 50, 57

(56) References Cited

U.S. PATENT DOCUMENTS

| | | | | |
|---|---|---|---|---|
| 3,439,525 A | * | 4/1969 | Waterman et al. | 374/5 |
| 3,511,086 A | * | 5/1970 | Woodmansee | 374/5 |
| 3,744,295 A | * | 7/1973 | Allinikov | 374/5 |
| 5,015,950 A | * | 5/1991 | Rose et al. | 324/224 |
| 5,165,797 A | * | 11/1992 | Kuroda et al. | 374/162 |
| 5,298,433 A | | 3/1994 | Furuyama | |
| 5,764,650 A | | 6/1998 | Debenham | |
| 6,138,256 A | | 10/2000 | Debenham | |
| 6,219,810 B1 | | 4/2001 | Debenham | |
| 6,321,353 B2 | | 11/2001 | Debenham | |
| 6,523,144 B2 | | 2/2003 | Debenham | |
| 2002/0031164 A1 | * | 3/2002 | Scheidt et al. | 374/7 |
| 2003/0165178 A1 | * | 9/2003 | Borden et al. | 374/5 |

* cited by examiner

*Primary Examiner*—Christopher W. Fulton
*Assistant Examiner*—Madeline Gonzalez
(74) *Attorney, Agent, or Firm*—Robert A Voigt, Jr.; Winstead Sechrest & Minick P.C.

(57) ABSTRACT

A method and semiconductor device for detecting a heat generating failure in an unpassivated semiconductor device. The semiconductor device has an unpassivated surface and a heat generating failure, e.g., short circuit. A coating may be applied to the unpassivated surface of the semiconductor device. The coating may be non-electrically conducting and capable of localizing heat generated by the failure in a particular area. The semiconductor device may be biased. The failure may then be detected by detecting a location of the heat generated by the failure in the coating.

10 Claims, 5 Drawing Sheets

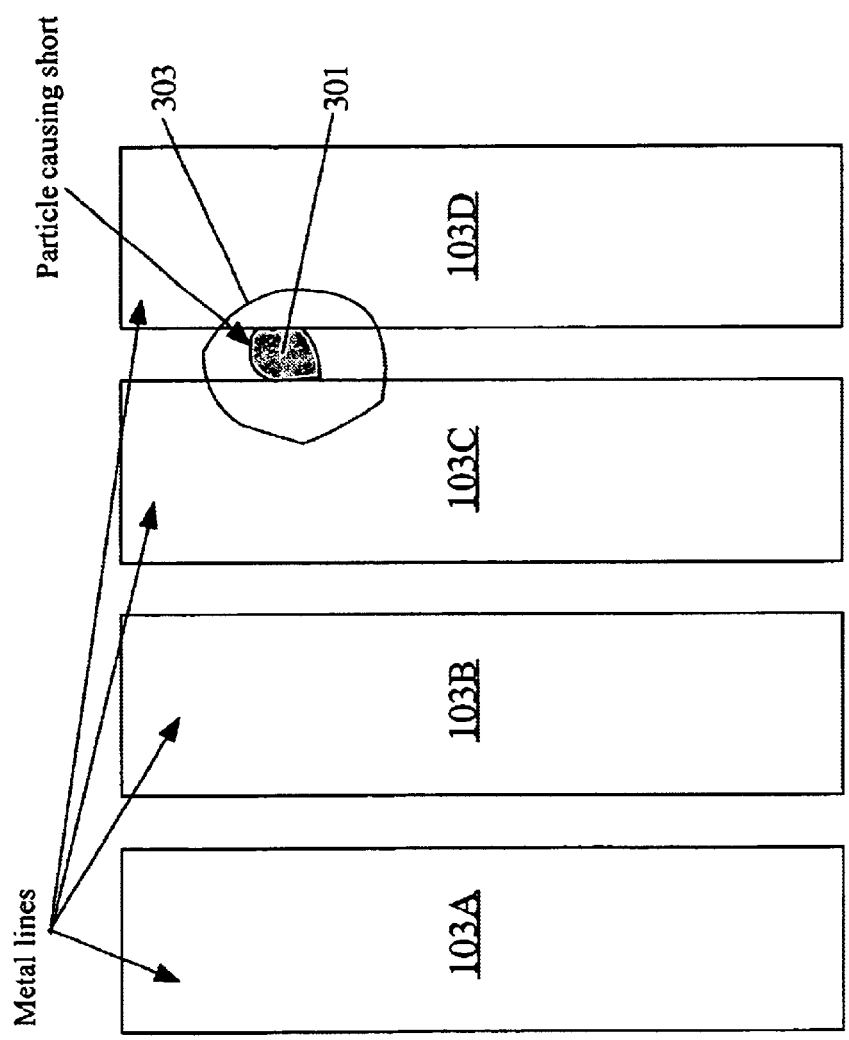
Figure 3C (Plan view)

DETECTING HEAT GENERATING FAILURES IN UNPASSIVATED SEMICONDUCTOR DEVICES

TECHNICAL FIELD

The present invention relates to the field of semiconductor devices, and more particularly to detecting heat generating failures in an unpassivated semiconductor device (a semiconductor device with a surface not having a passivation layer) by placing a non-electrically conductive coating on the unpassivated surface.

BACKGROUND INFORMATION

Conventional semiconductor devices are fabricated with a large number of components. For example, a single semiconductor device may include a number of structures, such as gates, junctions, interconnects and contacts formed on an active area. The active area typically resides above a bulk silicon substrate of the semiconductor device. The structures formed may be desired to be electrically isolated. For example, although interconnects are designed to electrically connect certain portions of the semiconductor device, interconnects may be electrically isolated from the other interconnects. In another example, a floating gate may be electrically insulated from the source and drain.

Semiconductor devices may experience failures, such as shorts, that arise when the semiconductor device is fabricated. Similarly, components of the semiconductor devices may fail during testing and/or operation. Hence, it may be desirable to perform failure analysis on semiconductor devices to determine if a failure occurred and if so, what type of failure has occurred, whether any of the components were affected and the location of the failure.

Certain types of failures, such as short circuits, generate heat. Hence, it may be desirable to detect such failures based upon the generation of heat. Detecting such failures based upon the generation of heat may be accomplished for semiconductor devices that have passivation layers on their surfaces. A passivation layer may refer to a layer on the surface of the semiconductor device that protects silicon structures from contamination. Failures, e.g., short Circuit, that generate heat may be detected beneath such a passivation layer because the heat will not be dissipated but localized around the source of the failure. Consequently, by detecting heat generated in a particular area of the semiconductor device, one may be able to detect and locate the source of a failure.

However, some semiconductor devices do not have a passivation layer on a surface of the semiconductor device. These types of semiconductor devices may be referred to as "unpassivated semiconductor devices." For example, an unpassivated surface may include a surface of the semiconductor device that has been exposed by removing a portion of the bulk silicon substrate of the semiconductor device. Since an unpassivated semiconductor device has a surface that is unpassivated, heat that may be generated from a failure, e.g., short circuit, may be dissipated thereby preventing the detection of the failure.

Therefore, there is a need in the art to be able to detect heat generating failures in unpassivated semiconductor devices.

SUMMARY

The problems outlined above may at least in part be solved in some embodiments by applying a non-electrically conductive coating to an unpassivated surface of the unpassivated semiconductor device thereby being able to localize the heat generated by a failure in the unpassivated semiconductor device.

In one embodiment of the present invention, a method for detecting a heat generating failure in a semiconductor device having an unpassivated surface may comprise the step of applying a non-electrically conductive coating to the unpassivated surface of the semiconductor device where the coating is capable of localizing heat generated by a heat-generating failure. The semiconductor device may be biased. The failure may be located by determining the location of the heat in the coating.

The foregoing has outlined rather broadly the features and technical advantages of one or more embodiments of the present invention in order that the detailed description of the invention that follows may be better understood. Additional features and advantages of the invention will be described hereinafter which form the subject of the claims of the invention.

BRIEF DESCRIPTION OF THE DRAWINGS

A better understanding of the present invention can be obtained when the following detailed description is considered in conjunction with the following drawings, in which:

FIG. 3C is a plan view of the unpassivated semiconductor device after the step of biasing the unpassivated semiconductor device is performed in accordance with the present invention.

DETAILED DESCRIPTION

The present invention comprises a method and semiconductor device for detecting a heat generating failure in a semiconductor device having an unpassivated surface. A non-electrically conductive coating may be applied to the unpassivated surface of the semiconductor device where the coating may be capable of localizing heat generated by a heat-generating failure. The semiconductor device may be biased. Upon biasing the semiconductor device, a heat generating failure may be located by determining the location of the heat in the coating.

It is noted that the present invention relates to an improvement in failure analysis of semiconductor devices, particularly semiconductor devices having an unpassivated surface. The following description is presented to enable one of ordinary skill in the art to make and use the invention and is provided in the context of a patent application and its requirements. Various modifications to the disclosed embodiments will be readily apparent to those skilled in the art and the generic principles discussed herein may be applied to other embodiments. Thus, the present invention is not intended to be limited to the embodiment shown, but is to be accorded the widest scope consistent with the principles and features described herein.

It is further noted that the present invention will be described in terms of a particular unpassivated semiconductor device. However, the present invention is consistent with the testing of other semiconductor devices. One of ordinary skill in the art will also readily recognize that for clarity, only certain portions of the semiconductor devices are depicted.

Figure 1:
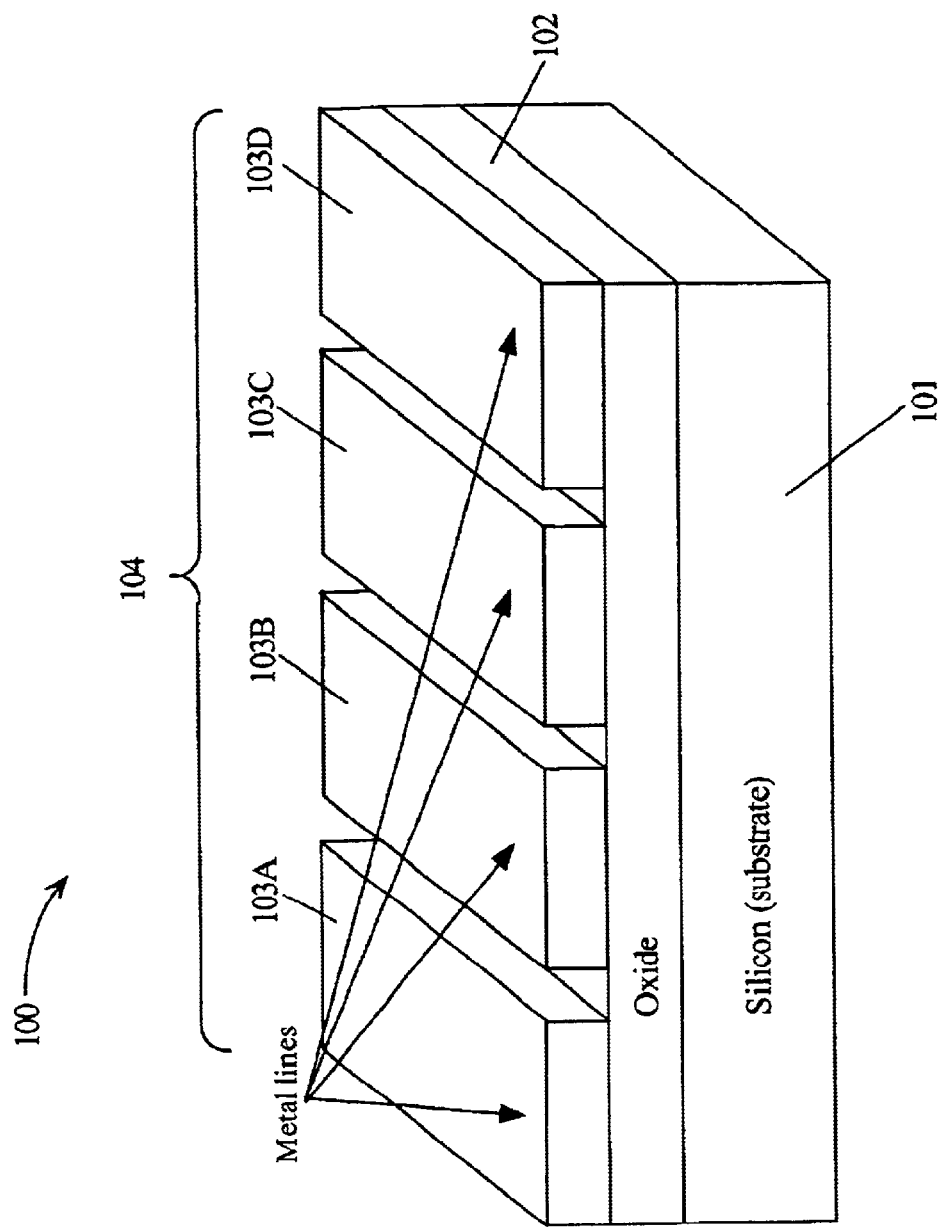
FIG. 1 is a side view of an embodiment of the present invention of an unpassivated semiconductor device.

FIG. 1—Semiconductor Device

FIG. 1 illustrates an embodiment of the present invention of an unpassivated semiconductor device 100. It is noted that for clarity, that only the portion of semiconductor device 100 is depicted and that FIG. 1 is illustrative. Referring to FIG. 1, semiconductor device 100 may comprise bulk silicon 101, which acts as a substrate. Semiconductor device 100 may further comprise an oxide layer 102 residing on silicon 101. Semiconductor device 100 may further comprise a plurality of metal lines 103A–D residing on oxide layer 102. Metal lines 103A–D may collectively or individually be referred to as metal lines 103 or metal line 103, respectively. It is noted that semiconductor device 100 may comprise any number of metal lines 103 and that FIG. 1 is illustrative.

As illustrated in FIG. 1, semiconductor device 100 does not have a passivation layer on its surface 104 thereby exposing metal lines 103 to the air. Hence, semiconductor device 100 may be referred to as an "unpassivated" semiconductor device. As discussed in the Background Information section, since an unpassivated semiconductor device has a surface that is exposed to the air, heat that may be generated from a failure, e.g., short circuit, may be dissipated in the air thereby preventing the detection of the failure. Therefore, there is a need in the art to be able to detect heat generating failures in unpassivated semiconductor devices.

Figure 2:
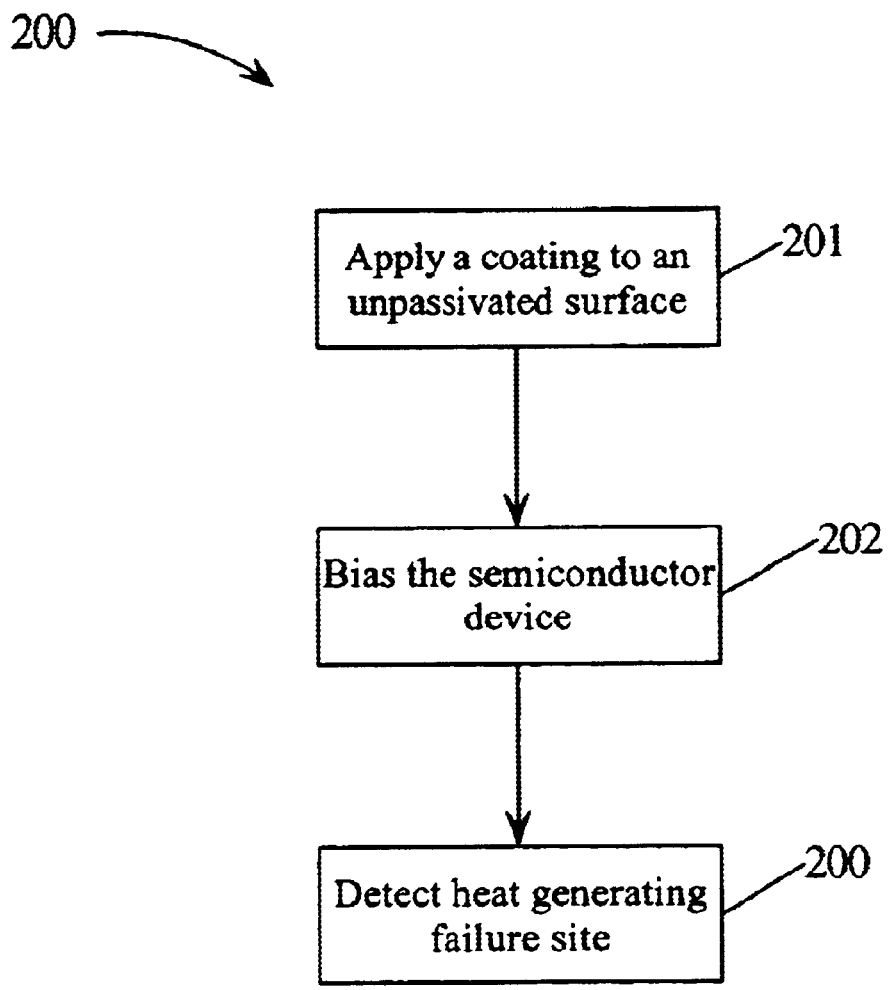
FIG. 2 is a flowchart of a method for detecting heat generating failures in unpassivated semiconductor devices in accordance with the present invention.
Figure 3A:
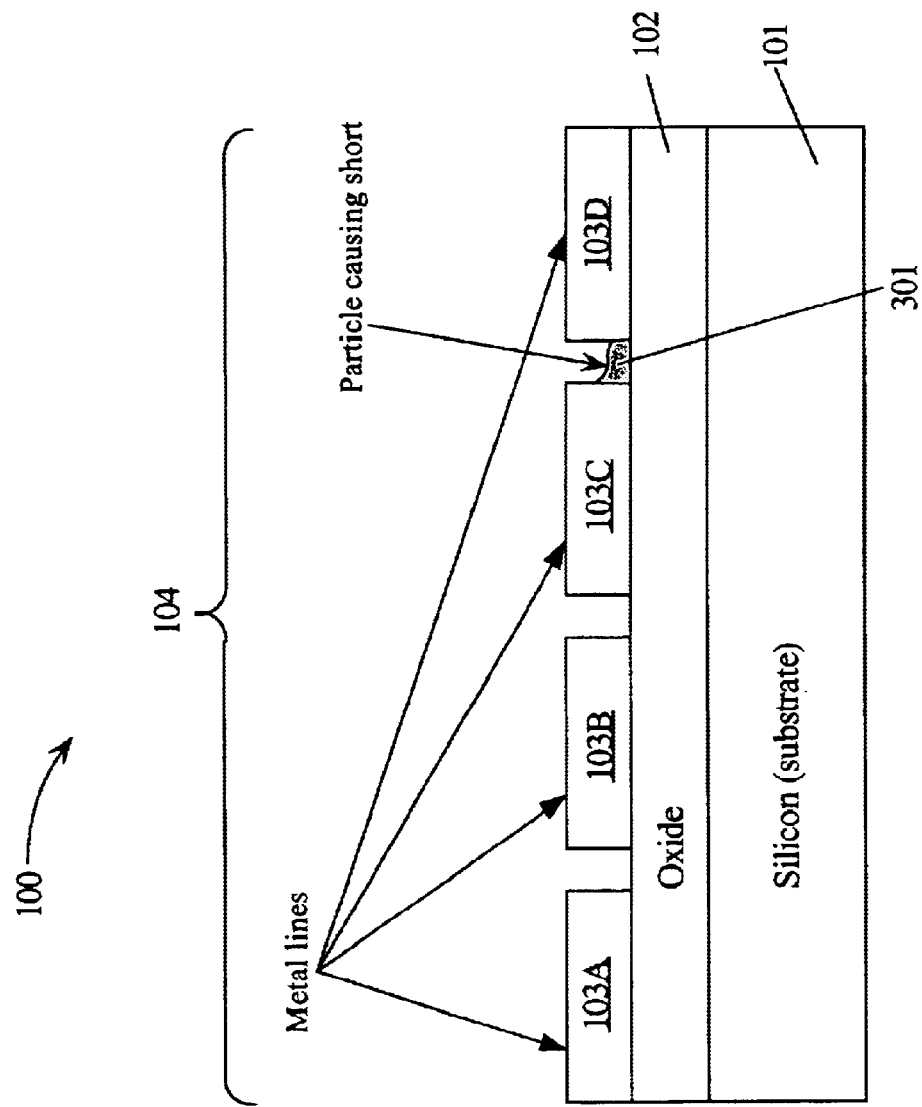
FIG. 3A is a cross-sectional view of the unpassivated semiconductor having a heat generating failure in accordance with the present invention.
Figure 3B:
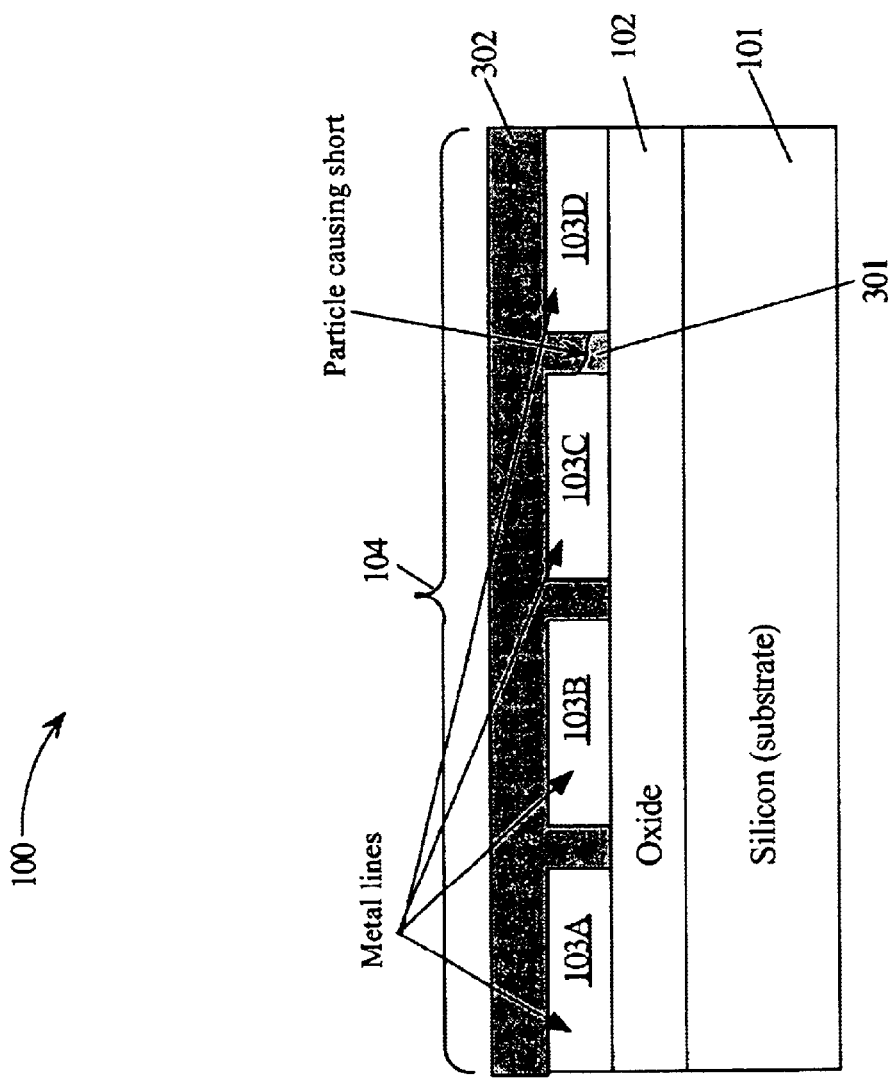
FIG. 3B is a cross-sectional view of the unpassivated semiconductor device after the step of applying a non-electrically conductive coating on an unpassivated surface of the unpassivated semiconductor device is performed in accordance with the present invention.

Heat generating failures may be detected in unpassivated semiconductor devices by applying a non-electrically conductive coating to an unpassivated surface as discussed below in conjunction with FIGS. 2 and 3A–C. FIG. 2 is a method for detecting heat generating failures in unpassivated semiconductor devices. FIG. 3A is a cross-sectional view of an unpassivated semiconductor having a heat generating failure, e.g., short circuit. FIG. 3B is a cross-sectional view of the unpassivated semiconductor device after the step of applying a non-electrically conductive coating on an unpassivated surface of the semiconductor device is performed in the method described in FIG. 2. FIG. 3C is a plan view of the unpassivated semiconductor device after the step of biasing the semiconductor device is performed in the method described in FIG. 2.

FIG. 2—Method for Detecting Heat Generating failures in an Unpassivated Semiconductor Device FIG. 2 is a flowchart of one embodiment of the present invention of a method 200 for detecting heat generating failures in semiconductor device 100 (FIG. 1) having an unpassivated surface 104 (FIG. 1).

Referring to FIG. 3A, FIG. 3A illustrates an embodiment of semiconductor device 100 of FIG. 1 comprising a heat generating failure 301, e.g., short circuit, to be detected using method 200. Referring to FIG. 2, in conjunction with FIG. 3A, in step 201, a coating is applied to unpassivated surface 104. The coating may be electrically insulating and allow for heat generated in the underlying semiconductor device to be localized in a small region of the coating. Thus, the coating may be thermally conductive. In addition, the coating may not allow heat to readily dissipate from unpassivated surface 104 of semiconductor device 100. In one embodiment, the coating used in step 201 may be a thin layer of liquid. For example, liquids that are thermally conductive but not electrically conductive, which have a high flash point to prevent burning of the coating and a low vapor pressure to prevent rapid evaporation of the liquid, may be used. In addition, the coating need not be liquid. In one embodiment, a silicon dioxide coating may be deposited on unpassivated surface 104 of semiconductor device 100 in step 201. For example, a Focused Ion Beam (FIB) may be used to deposit a coating of silicon dioxide. In such an embodiment, it may be preferred that the coating be approximately two microns in thickness.

Referring to FIG. 3B, FIG. 3B is a cross-sectional view of semiconductor device 100 after step 201 has been performed. As illustrated in FIG. 3B, a coating 302 may be applied to unpassivated surface 104 of semiconductor device 100. Coating 302 may be a thin coating of liquid. In another embodiment, coating 302 may be silicon dioxide or another suitable material.

Returning to FIG. 2 in conjunction with FIG. 3B, in step 202, semiconductor device 100 is biased thereby causing failure 301 to generate heat. Referring to FIG. 3C, FIG. 3C is a plan-view of semiconductor device 100 after step 202 has been performed. As illustrated in FIG. 3C, region 303 refers to a region in coating 302 (FIG. 3B) in which heat is being generated from failure 301.

Returning to FIG. 2, in conjunction with FIGS. 3B–C, the heat generating failure 301 is detected by detecting the failure site (site where failure occurs) or at least the localized area of the heat (region 303) in coating 302 generated from failure 301 in step 203. Step 203 may include detecting hot spots using an infrared or other heat sensor. Such sensors are often provided with tools typically used in failure analysis, such as a Mercury Cadmium Telluride (also known as MERCAD) detector or emission microscope. Because coating 302 localizes and reduces the amount of heat dissipated, the tool used in step 203 has an opportunity to capture the heat generated.

Thus, using method 200, heat can be used to detect the location of heat-generating failures, even for unpassivated semiconductor device 100. Thus, failures, such as shorts 301, may be detected without requiring the experimenter to deprocess the entire semiconductor device 100 in an effort to search for the failure. Once failure 301 has been located using method 200, the region immediately around the failure can be deprocessed to further investigate the nature of failure 301. As a result, failure analysis is improved and expedited.

It is noted that one of ordinary skill in the art will readily recognize that method 200 may include other and/or additional steps that, for clarity, are not depicted. It is further noted that method 200 may be executed in a different order presented and that the order presented in the discussion of FIG. 2 is illustrative.

A method and system has been disclosed for detecting heat generating failures in a semiconductor device having an unpassivated surface. Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims. It is noted that the headings are used only for organizational purposes and not meant to limit the scope of the description or claims.

What is claimed is:

1. A method for detecting a heat generating failure in a semiconductor device having an unpassivated surface comprising the steps of:

applying a coating to said unpassivated surface of said semiconductor device, wherein said coating is non-electrically conducting and capable of localizing heat generated by said failure in a particular area;

biasing said semiconductor device; and detecting said failure by detecting a location of said heat generated by said failure in said coating.

2. The method as recited in claim 1, wherein said coating comprises a high flash point and a low vapor pressure.

3. The method as recited in claim 1, wherein said coating comprises a liquid.

4. The method as recited in claim 1, wherein said coating comprises silicon dioxide.

5. The method as recited in claim 4, wherein said coating has a thickness of approximately two microns.

6. A semiconductor device comprising:

an unpassivated surface; and a coating on said unpassivated surface, wherein said coating is non-electrically conducting and capable of localizing heat generated by a failure in a particular area of said coating, wherein said failure is detected by detecting a location of said heat generated by said failure in said coating.

7. The semiconductor device as recited in claim 6, wherein said coating comprises a high flash point and a low vapor pressure.

8. The semiconductor device as recited in claim 6, wherein said coating comprises a liquid.

9. The semiconductor device as recited in claim 6, wherein said coating comprises silicon dioxide.

10. The semiconductor device as recited in claim 9, wherein said coating has a thickness of approximately two microns.

* * * * *